United States Patent
Yoneya et al.

[11] Patent Number: 5,557,349
[45] Date of Patent: Sep. 17, 1996

[54] FUNDUS CAMERA FOR INFRARED FLUORSEIN ANGIOGRAPHY

[75] Inventors: Shin Yoneya, Maebashi; Masayuki Takasu, Tokyo-to, both of Japan

[73] Assignee: Kabushiki Kaisha TOPCON, Tokyo-to, Japan

[21] Appl. No.: 372,223

[22] Filed: Jan. 13, 1995

[51] Int. Cl.⁶ .................................................. A61B 3/14
[52] U.S. Cl. .................................... 351/206; 351/213
[58] Field of Search ............................ 351/206, 213, 351/221

[56] References Cited

U.S. PATENT DOCUMENTS

| | | | |
|---|---|---|---|
| 4,854,692 | 8/1989 | Kobayashi | 351/221 |
| 5,118,179 | 6/1992 | Sano et al. | 351/206 |
| 5,181,055 | 1/1993 | Sano et al. | 351/206 |
| 5,214,454 | 5/1993 | Sano | 351/221 |
| 5,287,129 | 2/1994 | Sano et al. | 351/213 |
| 5,291,231 | 3/1994 | Hideshima et al. | 351/206 |

FOREIGN PATENT DOCUMENTS

| | | | |
|---|---|---|---|
| 4132181 | 3/1992 | Germany | 351/206 |
| 4141087 | 6/1992 | Germany | 351/206 |
| 484931 | 3/1992 | Japan | 351/213 |

*Primary Examiner*—William L. Sikes
*Assistant Examiner*—James A. Dudek
*Attorney, Agent, or Firm*—Nields & Lemack

[57] ABSTRACT

The present invention relates to a fundus camera for photographing vascular condition of the retina in medical examination for checking health, and it comprises a retina illuminating system for projecting infrared illuminating light beam to the retina to be examined, a first barrier filter having a first transmission wavelength range and a second barrier filter having a second transmission wavelength range shifted toward longer wavelength range, said two barrier filters being interchangeable with each other, and a photographing system for angiography of the retina to be examined through either the first or the second barrier filters, whereby a proper fluorescent vascular image is photographed even when fluorescent light wavelength from the retina is changed with the lapse of time.

6 Claims, 3 Drawing Sheets

FUNDUS CAMERA FOR INFRARED FLUORSEIN ANGIOGRAPHY

BACKGROUND OF THE INVENTION

The present invention relates to a fundus camera (retinal camera), and in particular to a fundus camera, by which it is possible to achieve infrared fluoresein angiography.

Fundoscopy is one of the important medical examinations to check health condition, and it is to examine vascular conditions of the retina. A fundus camera is used for photographing the conditions of the retina. In recent years, there has been proposed a fundus camera, by which it is possible to perform infrared fluoresein angiography by injecting fluorescent dye into blood of the patient to be examined and by taking fluorescent vascular image using infrared light.

Description is now given on a conventional type fundus camera for infrared fluoresein angiography.

Into blood of the patient to be examined, indocyanine green (in the following, it is shown as ICG), a fluorescent dye having absorption peak at 780 nm in infrared range, is injected. As a light source for illuminating measuring light into the retina of the patient, a xenon lamp is generally used, and only infrared light is projected. Specifically, an exciter filter is provided on projection side, and it is to transmit the light of the wavelength range to be absorbed in ICG and to cut light with longer wavelength. Infrared light is irradiated through this exciter filter. As shown in FIG. 2 by the curve 27a, ICG in blood absorbs infrared light having a peak at 780 nm, and fluorescent light having central wavelength of 810 nm as shown by the curve 28a in FIG. 2 is irradiated. A barrier filter is installed on light receiving side, and this transmits the light in fluorescent light wavelength range and shuts off light with shorter wavelength. As a result, only fluorescent light is received, and an image of retina blood vessels can be photographed at high resolution.

On the other hand, if albumin in blood is bonded to ICG at a certain period of time (about 30 seconds) after injection of ICG, the peak of absorption wavelength is changed from 780 nm to 805 nm as shown by the curve 27b in FIG. 2. At the same time, the peak of fluorescent light wavelength is also changed to 835 nm as shown by the curve 28b in FIG. 2.

Therefore, it is not possible to photograph with high resolution when a certain period of time has elapsed.

Taking such change of fluorescent light wavelength into account, a fundus camera has been proposed. In this camera, the exciter filter and the barrier filter are installed to match wavelength range after a certain period of time has elapsed in order to photograph the image of retina.

One of the advantages of infrared fluorescent angiography is the possibility to identify behavior of blood with a fluorescent dye injected into it. In the infrared fluoresein angiography, continuous photographing of moving images with the lapse of time or continuous photographing of numerous static images are performed with the lapse of time in order to record the change of the condition from injection of the fluorescent dye.

In the former case among the conventional cases, proper angiography can be achieved in initial stage when binding of albumin in blood with ICG is not started yet. But, when the peak of absorption wavelength and fluorescent light wavelength is deviated to longer wavelength after the binding of albumin with ICG, irradiation light beam is shut off by the exciter filter, and illumination light, i.e. fluorescent light, is shut off by the barrier filter, and this makes it impossible to perform effective angiography after a certain period of time.

Among the conventional cases, proper angiography can be achieved after a certain period of time in the latter case, while effective angiography cannot be performed in the initial condition, inconveniently.

SUMMARY OF THE INVENTION

Thus, it is an object of the present invention to provide a fundus camera, by which it is possible to photograph the retina conditions in effective manner not only under initial condition but also at a certain period of time after injection of the fluorescent dye. To attain the object, the fundus camera according to the present invention comprises a retina illuminating system for projecting infrared illumination light beam to the retina to be examined, a first barrier filter having a first transmission wavelength range and a second barrier filter having a second transmission wavelength range shifted toward longer wavelength with respect to the first transmission wavelength range, said two barrier filters being interchangeable with each other, and a photographing system for angiography of the retina to be examined through either the first or the second barrier filters.

DETAILED DESCRIPTION OF THE PREFERRED EMBODIMENTS

Figure 1:
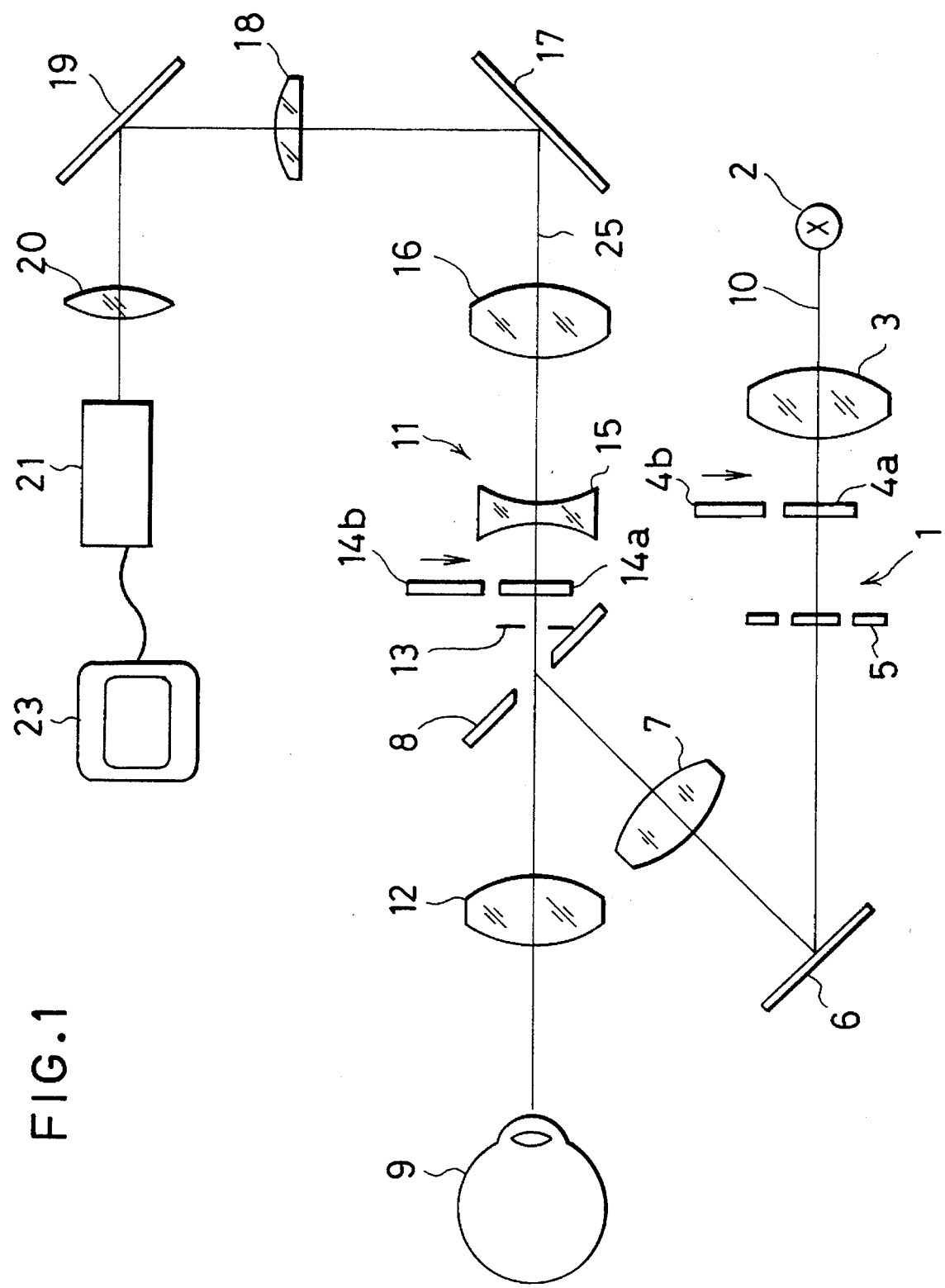
FIG. 1 represents a basic configuration of an embodiment of the present invention.
Figure 2:
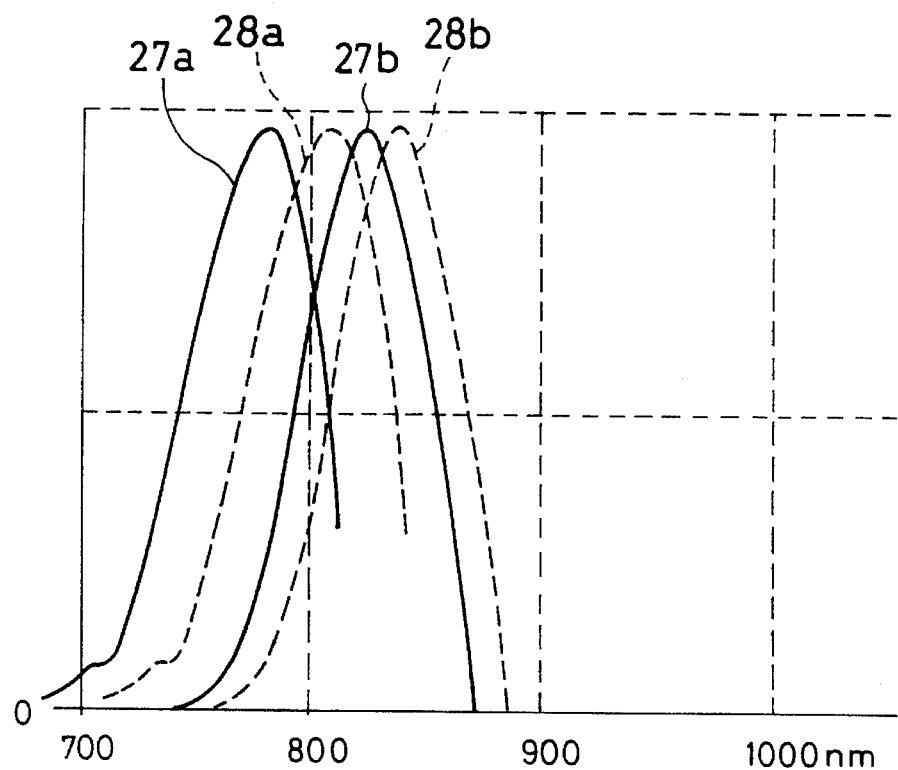
FIG. 2 is a diagram showing absorption characteristics of a fluorescent dye.

In FIG. 1, a retina illuminating system 1 comprises a xenon light source 2 used for photographing, a condenser lens 3, exciter filters, 4a and 4b, a ring diaphragm 5 with a ring hole perforated in it, a reflection mirror 6, a relay lens 7, and a perforated mirror 8 with a transmission hole formed at its center. Illumination light beam coming from the xenon light source 2 is limited to infrared light, and it is projected on the retina to be examined 9 as a ring light beam by the ring diaphragm 5. The ring diaphragm 5 and a pupil of the eye to be examined 9 are arranged at conjugate positions.

The exciter filters 4a and 4b are provided in such manner that they are interchangeable each other with respect to optical axis 10 of the retina illuminating system 1. The exciter filter 4a transmits infrared light with wavelength peak at 780 nm to be absorbed by ICG and with wavelength near the peak, and shuts off the light with longer wavelength. Transmission characteristics of the exciter filter 4a is represented by the curve 24a in FIG. 3. The exciter filter 4a with such transmission characteristics effectively transmits infrared light with wavelength peak at 780 nm to be absorbed by ICG and with wavelength near the peak, while it does not transmit infrared light with wavelength at 820 nm and near.

Figure 3:
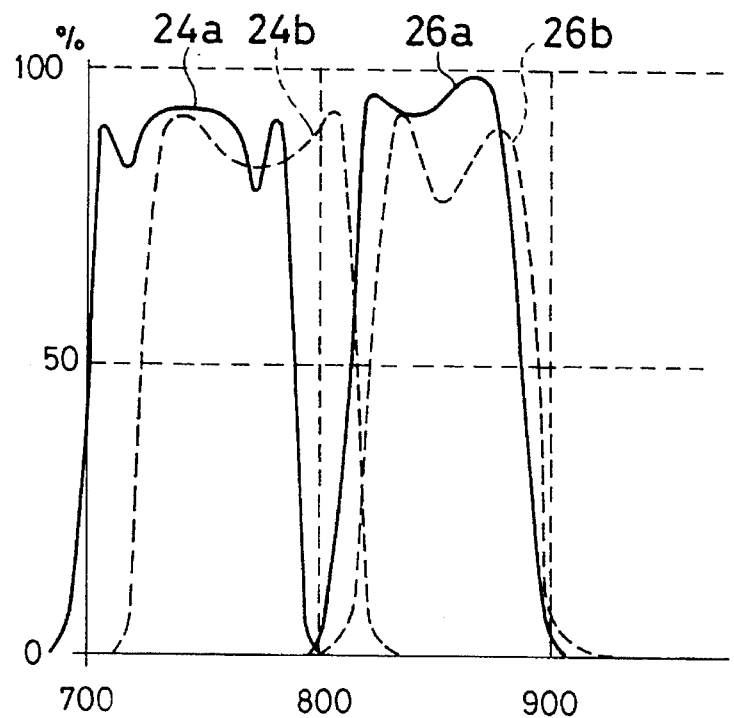
FIG. 3 is a diagram showing transmission characteristics of a filter.

Transmission characteristics of the exciter filter 4b is given by the curve 24b in FIG. 3. As shown by the curve 24b in FIG. 3, the exciter filter 4b with such transmission characteristics transmits infrared light at 805 nm and near, which is the peak of the wavelength to be absorbed when albumin is bonded to ICG, but it does not transmit infrared light with wavelength at 835 nm and near.

The exciter filter 4a and the exciter filter 4b are moved in linked manner. Although not shown in the figure, driving means such as solenoid is connected, and a timer is provided in driving circuit of the driving means so that the exciter filters 4a and 4b are interchanged after a certain period of time.

A photographing system 11 comprises an object lens 12, a photographing diaphragm 13, barrier filters 14a and 14b, a focusing lens 15, an imaging lens 16, a reflection mirror 17, a field lens 18, a reflection mirror 19, a relay lens 20, and a pickup tube 21. Output from the pickup tube 21 is displayed on a monitor television 23. The photographing diaphragm 13 and a pupil of the eye to be examined 9 are arranged at conjugate positions.

The photographing diaphragm 13 shuts off ring-like reflection light reflected at cornea and transmits only the photographing light beam from the retina.

The barrier filters 14a and 14b are arranged interchangeably with each other with respect to an optical axis 25 of the photographing system 11. The barrier filter 14a has a transmission curve similar to the curve 26a in FIG. 3 and it transmits infrared light at the peak wavelength of fluorescent light, i.e. 820 nm and near, and it shuts off infrared light with shorter wavelength. Therefore, photographing light beam from the retina is shut off, and only fluorescent light passes through it.

The barrier filter 14b has a transmission curve similar to the curve 26b in FIG. 3, and it transmits infrared light at the peak wavelength of fluorescent light, i.e. 835 nm and near, and shuts off infrared light with shorter wavelength. Accordingly, only the fluorescent light irradiated when albumin is bonded to ICG is transmitted and other light reflected from the retina is shut off.

The barrier filters 14a and 14b are moved in linked manner. Although not shown in the figure, driving means such as solenoid is connected. A timer is provided in driving circuit of the driving means so that the barrier filters 14a and 14b are interchanged with each other after a certain period of time.

In the initial stage of the examination, the exciter filter 4a and the barrier filter 14a are arranged on optical axis, and after a certain period of time has elapsed, these are replaced with the exciter filter 4b and the barrier filter 14b. Then, it is possible to photograph under proper condition by fluorescent light only from initial stage to the completion of the examination even when absorption characteristics of the fluorescent dye are changed with the lapse of time, and an image with high resolution can be obtained. As a result, dynamic fundoscopy with high precision can be achieved as time elapses.

Figure 4:
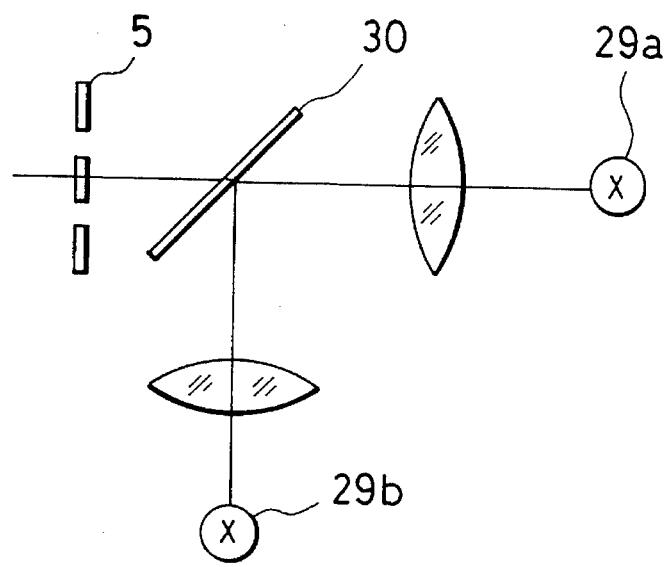
FIG. 4 drawing for explaining a light source of another embodiment of the invention.

In the above embodiment, a xenon light source is used, while a laser light source, i.e. a single wavelength light source, may be used, and two types of wavelengths may be irradiated from the laser light source. For example, as shown in FIG. 4, there are provided a laser light source 29a emitting infrared light of 780 nm and a laser light source 29b emitting infrared light of 805 nm, and the light from the laser light sources 29a and 29b are guided to the eye to be examined 9 by a half mirror 30. In the initial stage of examination, the laser light source 29a is turned on and infrared light from the laser light source 29a is irradiated. After a certain period of time has elapsed, the laser light source 29a is turned off, and the laser light source 29b is turned on, and infrared light from the laser light source 29b is irradiated.

Figure 5:
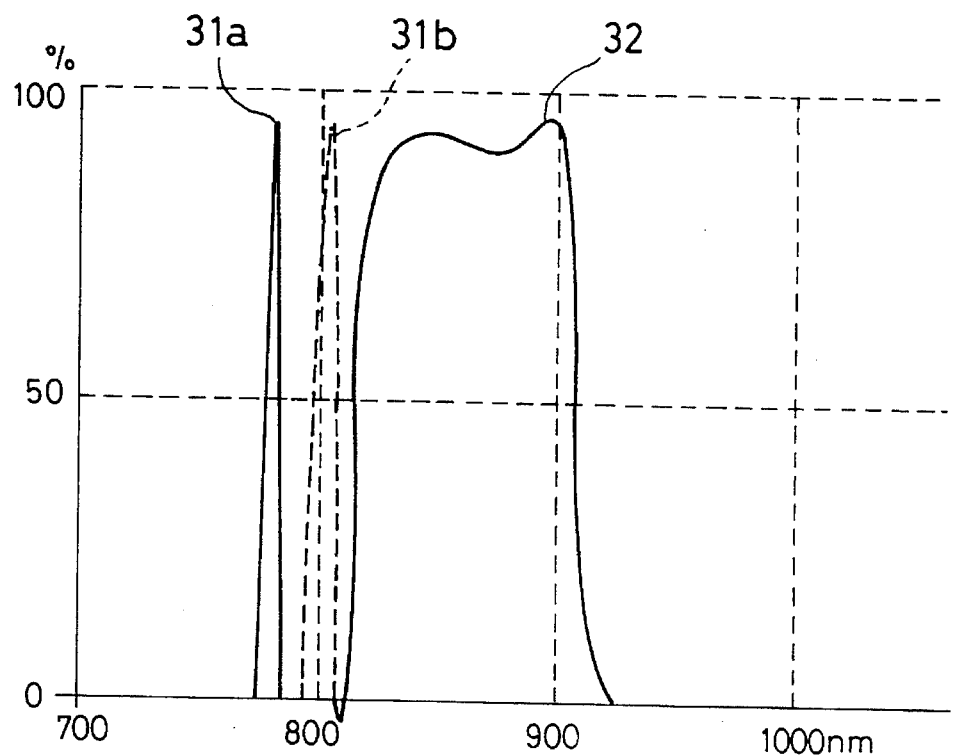
FIG. 5 is a diagram showing light emission characteristics of a laser illumination and transmission characteristics of a filter in said another embodiment of the invention.

In FIG. 5 the curve 31a represents infrared light emitted from the laser light source 29a, and the curve 31b represents infrared light emitted from the laser light source 29b. In the present embodiment, the same barrier filter as the above two barrier filters 14a and 14b may be used, or as shown by the curve 32 in FIG. 5, a single type of barrier filter may be used, which transmits the light with wavelength of 820 nm and 835 nm and shuts off infrared light with wavelength shorter than 805 nm and near.

Emission wavelength is changed by changing light emitting condition of laser light source. Therefore, two types of wavelengths may be emitted using the same laser light source, for example, by controlling temperature, which is one of the light emitting conditions. It is needless to say that a CCD camera may be used as pickup means instead of the pickup tube.

What we claim are:

1. A fundus camera, comprising a retina illuminating system for projecting infrared illuminating light beam to the retina to be examined, a first barrier filter having a first transmission wavelength range in the infrared wavelength range and a second barrier filter having a second transmission wavelength range in the infrared wavelength range shifted toward longer wavelength with respect to the first transmission wavelength range, said first and said second barrier filters being interchangeable with each other, and a photographing system for angiography of the retina to be examined through either the first or the second barrier filters, said first and said second barrier filters being arranged in said photographing system.

2. A fundus camera according to claim 1, wherein the retina illuminating system comprises a light source for emitting white light, a first exciter filter to transmit a third specific infrared wavelength range and a second exciter filter to transmit a fourth infrared specific wavelength range shifted toward longer wavelength with respect to the third specific infrared wavelength range, said first and second exciter filters being arranged in said retina illuminating system, and infrared illuminating light beam is projected on the retina of the eye to be examined through either the first or the second exciter filters.

3. A fundus camera according to claim 1, wherein the the retina illuminating system comprises a laser light source for emitting laser light of the third specific infrared wavelength range and laser light of the fourth specific infrared wavelength range shifted toward longer wavelength with respect to the third specific infrared wavelength range.

4. A fundus camera according to claim 3, wherein temperature of the laser light source is controlled and laser light of the third specific infrared wavelength range and laser light of the fourth specific infrared wavelength range are selected to emit light.

5. A fundus camera according to claim 1, wherein the first transmission wavelength range is centered at 820 nm, and the second transmission wavelength range is centered at 835 nm.

6. A fundus camera according of one of claims 2 or 3, wherein the third transmission wavelength range is centered at 780 nm, and the fourth transmission wavelength range is centered at 805 nm.

* * * * *